US008645538B2

(12) United States Patent
Pan

(10) Patent No.: US 8,645,538 B2
(45) Date of Patent: Feb. 4, 2014

(54) SYSTEM AND METHOD FOR MONITORING OUTBREAK OF CONTAGIOUS DISEASES

(76) Inventor: Yang Pan, Singapore (SG)

(*) Notice: Subject to any disclaimer, the term of this patent is extended or adjusted under 35 U.S.C. 154(b) by 158 days.

(21) Appl. No.: 13/300,584

(22) Filed: Nov. 20, 2011

(65) Prior Publication Data
US 2013/0132572 A1    May 23, 2013

(51) Int. Cl.
G06F 15/173    (2006.01)
(52) U.S. Cl.
USPC ............................................. 709/225
(58) Field of Classification Search
USPC ........................... 709/225, 228, 230
See application file for complete search history.

(56) References Cited

U.S. PATENT DOCUMENTS 6,556,852 B1 *   4/2003  Schulze et al. .............. 600/323
7,993,266 B2     8/2011  Colston, Jr. et al.
2005/0113131 A1  5/2005  Lin et al.
2006/0036619 A1  2/2006  Fuerst et al.
2008/0279420 A1  11/2008 Masticola et al.
2011/0093249 A1* 4/2011  Holmes et al. ................ 703/6

* cited by examiner

Primary Examiner — Larry Donaghue
Assistant Examiner — Marshall McLeod

(57) ABSTRACT

A surveillance system for monitoring outbreak of a contagious disease is disclosed. The system comprises a handheld computing and communication device with a short range ad hoc networking device. Handheld devices carried by persons in contacting with the device carried by a user form an ad hoc communication network at a location. Identities of all devices in the ad hoc network are broadcasted through the network. The user's device receives the identities and stores the received data in a log file. The log file may be sent to a central station after the device receives an authorized signal during an outbreak event of the contagious disease. The device may further include a body temperature automatic measuring system. The user's body temperature trend file may be sent together with the log file.

18 Claims, 11 Drawing Sheets

SYSTEM AND METHOD FOR MONITORING OUTBREAK OF CONTAGIOUS DISEASES

CROSS-REFERENCE TO RELATED APPLICATIONS

Not applicable.

BACKGROUND

1. Field of Invention

This invention relates generally to an information collection system. More specifically, the invention describes a system and method for monitoring outbreak of contagious diseases.

2. Description of Prior Art

Current surveillance systems and methods to prevent the outbreak of contagious diseases rely on post-symptomatic reporting, and therefore are severely limited in what portion of the population they can treat or isolate before infection becomes widespread and uncontrollable. In general, individuals are most infectious when they first begin to develop symptoms. The infected individuals typically show symptoms of fever. Therefore, a surveillance solution to prevent diseases transmitted by person-to-person interaction before the specific disease becomes epidemic is greatly desired.

SUMMARY OF THE INVENTION

Accordingly, it is an objective of the present invention to provide a surveillance system for monitoring outbreak of a contagious disease through tracking person-to-person interaction by using handheld computing and communication devices.

It is another objective of the present invention to provide an automatic body temperature measuring system integrated with the handheld computing and communication device. Therefore, the body temperatures of potential infected individuals can be reported to an authorized central station automatically.

An exemplary system comprises a handheld computing and communication device with a short range ad hoc networking device. Handheld devices carried by persons in contacting with the device carried by a user form an ad hoc communication network at a location. Identities of the devices are transmitted to the user's device through the ad hoc network and are stored in a log file. The location of the user may be determined by a location determining device, such as for example, a GPS (Global Positioning System). The location may be stored in the same log file. The log file may be sent to an authorized central station after the device receives an authorized signal during outbreak of a contagious disease. The device may further include a body temperature automatic measurement system. A file including the user's body temperature trend may be sent together with the log file. The log file may also be sent to the central station automatically during an epidemic disease event if recorded body temperatures are exceeding a predetermined value.

BRIEF DESCRIPTION OF THE DRAWINGS

For a more complete understanding of the present invention and its various embodiments, and the advantages thereof, reference is now made to the following description taken in conjunction with the accompanying drawings, in which.

DETAILED DESCRIPTION

References will now be made in detail to a few embodiments of the invention, examples of which are illustrated in the accompanying drawings. While the invention will be described in conjunction with the particular embodiments, it will be understood that it is not intended to limit the invention to the described embodiments. To the contrary, it is intended to cover alternatives, modifications, and equivalents as may be included within the spirit and scope of invention as defined by the appended claims.

Figure 1A:
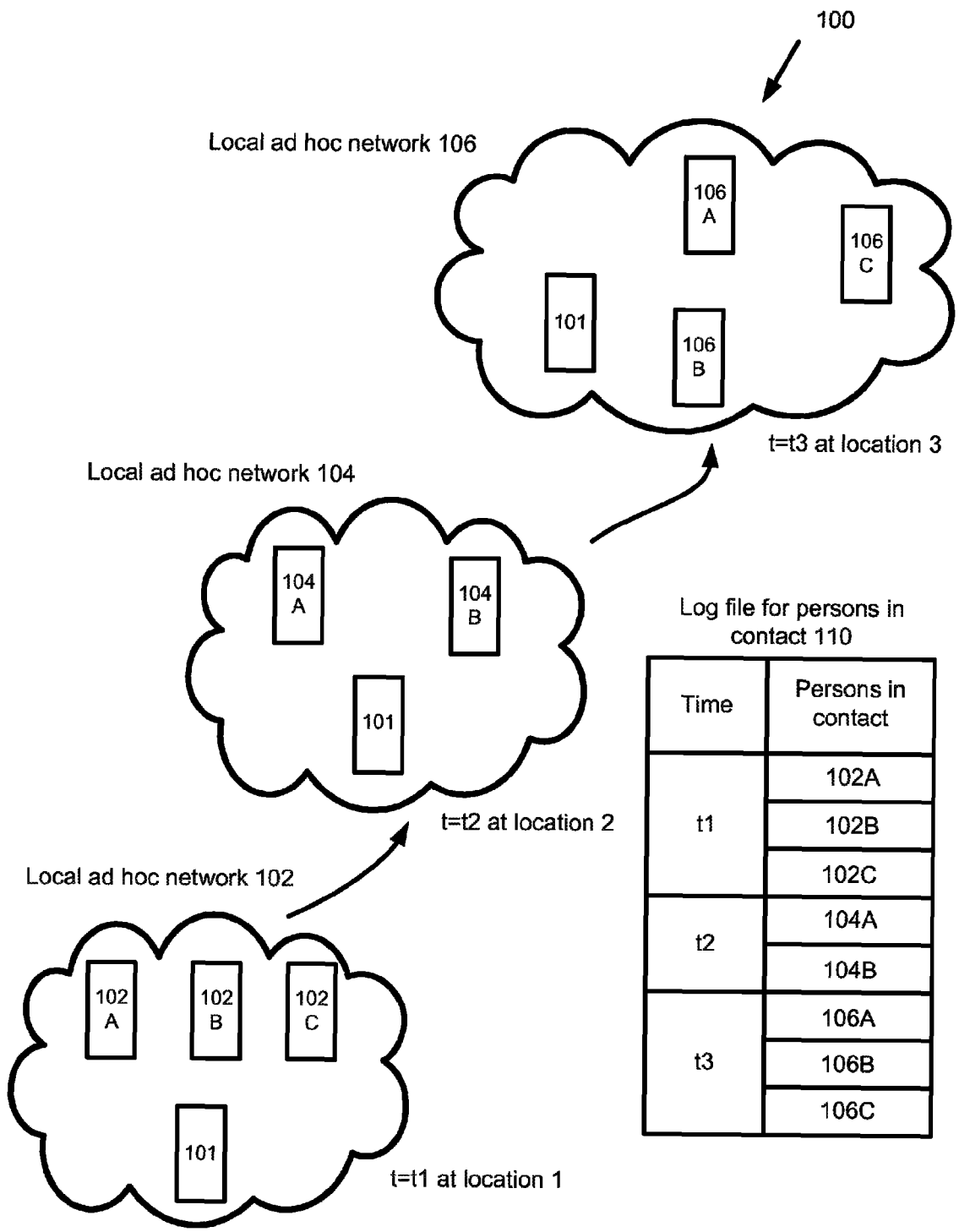
FIG. 1A is a schematic diagram illustrating an exemplary surveillance system based upon handheld computing and communication devices.

FIG. 1A is a schematic diagram illustrating an exemplary surveillance system 100 based upon handheld computing and communication devices. As shown in FIG. 1A, at a time t1, a handheld computing and communication device 101 carried by a user forms an ad hoc communication network 102 with handheld devices 102A, 102B and 102C carried by persons nearby the user. There may be more or less handheld devices in the network 102 depending on the number of persons nearby who carried the devices. The handheld devices may take various forms including but not limiting to mobile phones, media players, laptop computers, tablet computers and digital cameras. The handheld devices may include ad hoc networking devices that conform exemplarily to standards including but not limiting to the Bluetooth (IEEE 802.11b) and its extensions, the ZigBee (IEEE 802.15.4) and its extensions, the Wi-Fi (IEEE 802.11) and its extensions and the NFC (Near Field Communication). The networking devices may conform to one or a combination of the above-mentioned standards. According to an alternative implementation, the ad hoc wireless communication network may also be formed through optical means including employing visible and invisible light beams.

Upon formation of the ad hoc network 102, data can be transferred amongst the devices in the network. According to one aspect of the present invention, each of the handheld devices has an identity. The identities are broadcasted through the ad hoc network 102. Each of the handheld devices receives the identities of the other devices in the network and stores the data in a log file as shown exemplarily as a table 110. The table 110 may include the identities of the devices in the ad hoc network 102. The identity may be a code or a series of digitals stored in a file storage system of the handheld device. The identities of the handheld devices are preferably be encrypted. They may be decrypted by an authorized central station.

According to another aspect of the present invention, a coverage range of the ad hoc network 102 may be changeable by changing a setting of the networking devices by a program in the handheld devices. A changeable coverage range may be needed to tailor different type of contagious diseases. The changing of the setting may be triggered by receiving an authorized signal from the central station.

The number of devices in the network 102 may be increased if additional devices carried by additional individuals reach the range for the networking. The number of devices in the network 102 may be reduced if some of individuals move out of the range. According to another aspect of the present invention, durations of time that the persons in contact with the user at the location can also be measured and recorded in the log file.

As illustrated exemplarily in FIG. 1A, the user may move from location 1 to location 2 to form another ad hoc network 104 with devices 104A and 104B at another time t2. The user may further move from location 2 to location 3 at yet another time t3 to form yet another network 106 with devices 106A, 106B and 106C. At location 2 and location 3, the identities of the devices in the range of ad hoc networking are received by the device 101 and are stored in the log file 110.

The process of receiving and recording identities of the devices in the ad hoc network is repeatable for the device 101 at different locations and at different times. According to one aspect of the present invention, the log file stores identities of the devices in the ad hoc networks only for a predetermined period of time, such as for example, one week. The historical data may be removed from the log file or be stored in different files.

Figure 1B:
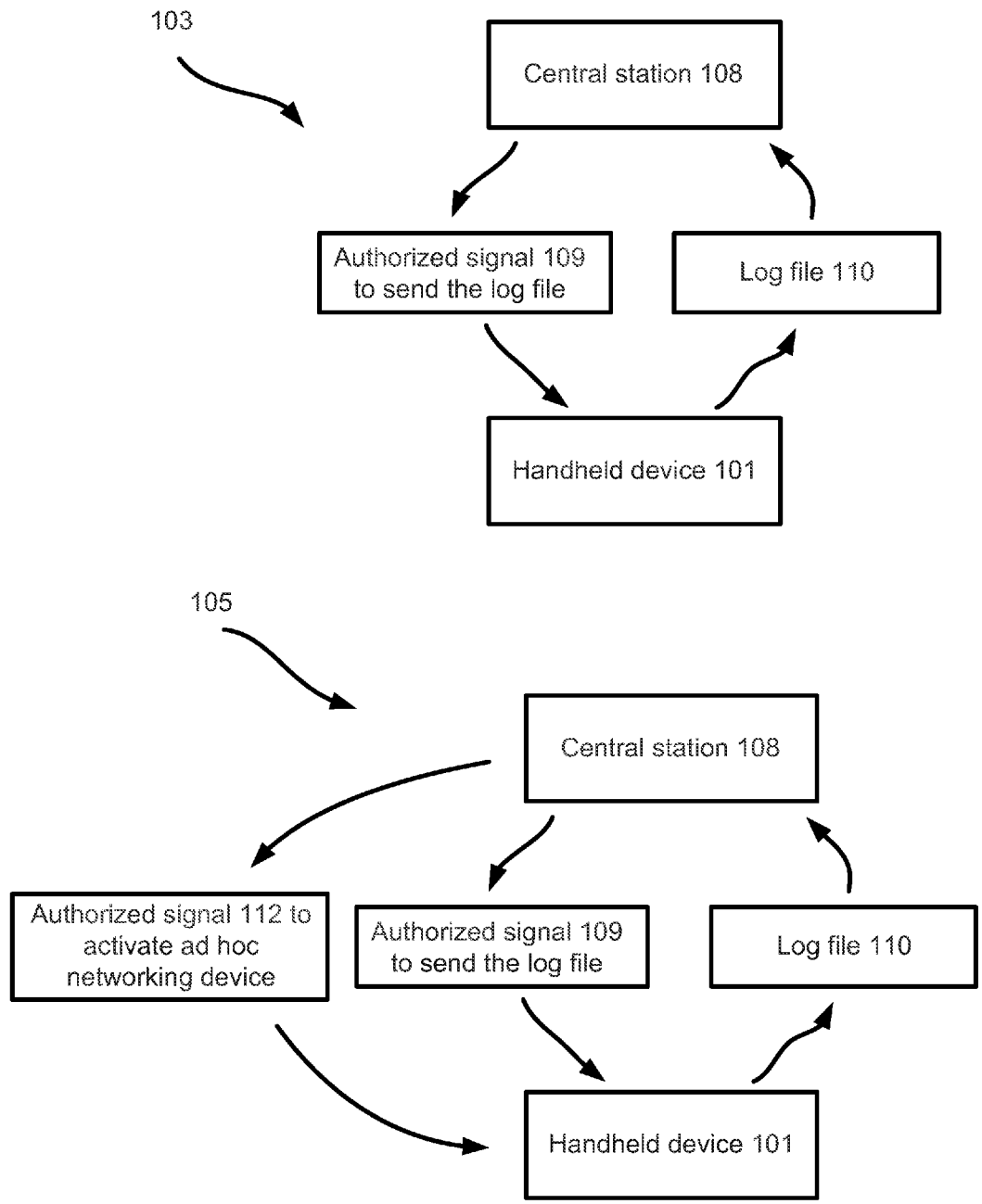
FIG. 1B-C is schematic diagram illustrating embodiments of the present invention.

FIG. 1B illustrates a first embodiment of the present invention in 103. The handheld device 101 is connected to a central station 108 through a communication network. The communication network may be a public telephone network. The communication network may also be the Internet. The device 101 receives an authorized signal 109 from the central station 108 to send the log file to the station. Upon receiving the authorized signal, the device 101 sends the log file 110 to the central station 108 through the communication network.

FIG. 1B further illustrates a second embodiment in 105. According to the embodiment, the ad hoc networking device is in a sleep mode under a normal operation condition of the device. The device 101 receives an authorized signal 112 from the central station 108 to activate the ad hoc networking device in the device. Because of general concerns about privacy, the central station 108 activates the function of tracking persons in contact only when there is an outbreak of a contagious disease.

According to one aspect of the present embodiment, the ad hoc networking device and other functional blocks of the device 101 may be switched on and off at the same time. According to another aspect, the ad hoc networking device and at least a part of the file storage function may be remaining as switching on when the power supply for the other functional blocks are switched off. According to yet another aspect, the ad hoc networking device and a part of file storage system may be remained as functional for a predetermined period of time after the other functional blocks are switched off. Such implementations are useful for the user in an airplane or in the theater. The part of the file storage system may comprise a cache.

Upon activating the ad hoc networking device, the device 101 receives and records identities of the devices in ad hoc networks at different locations and at different times. After receiving another authorized signal 109, the device 101 sends the log file 110 through the communication network to the central station 108.

Figure 1C:
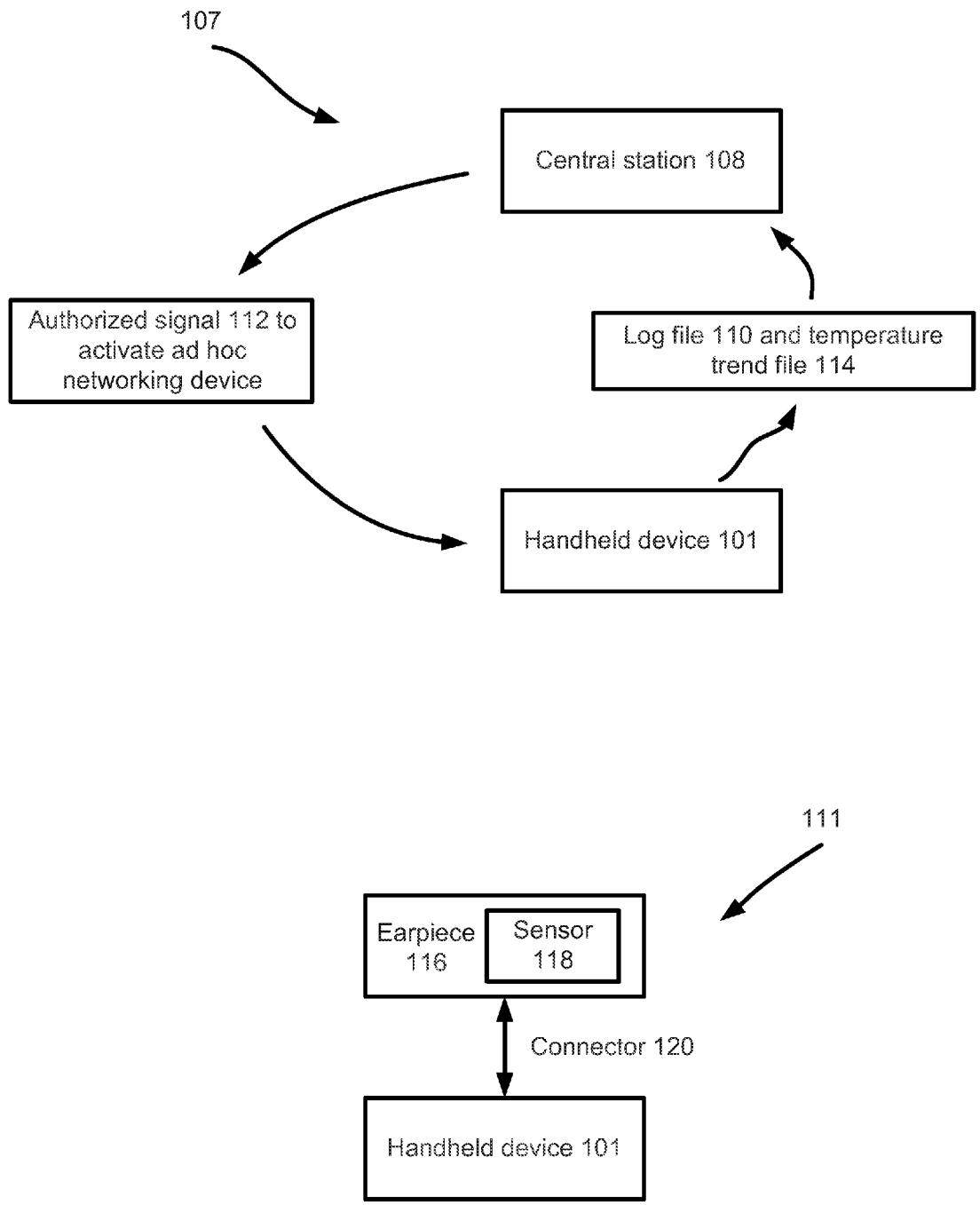

FIG. 1C illustrates a third embodiment in 107. After receiving the authorized signal 112 to activate the ad hoc networking device, the device 101 starts to receive and record identities of the devices in ad hoc networks. In the same time, a processor in the handheld device 101 initiates an automatic body temperature measuring system in the device 101 to measure the body temperatures of the user in a predetermined frequency.

An exemplary temperature measuring system is illustrated in 111. The handheld device 101 is connected to an earpiece 116 of the device through a connector 120. The connector 120 may be a wired connector. The connector 120 may also be a wireless connector, such as for example, a Bluetooth communication link. A temperature sensor 108 is placed in the earpiece 116. When the earpiece 116 is plugged into an ear of the user, the body temperature is taken. The body temperature may be taken automatically without the user's interactions. The measured temperatures and the times the temperatures are taken can be stored in a temperature trend file 114. The temperatures and the times may also be stored in the log file 110.

According to one aspect of the present embodiment, the log file 110 and the temperature trend file 114 may be sent to the central station 108 upon receiving the authorized signal 109. According to another aspect of the present embodiment, the log file 110 and the temperature trend file 114 may be sent to the central station 108, if any abnormality of the body temperature is detected such as if the body temperature is in exceeding of 37.5 C.

Figure 2A:
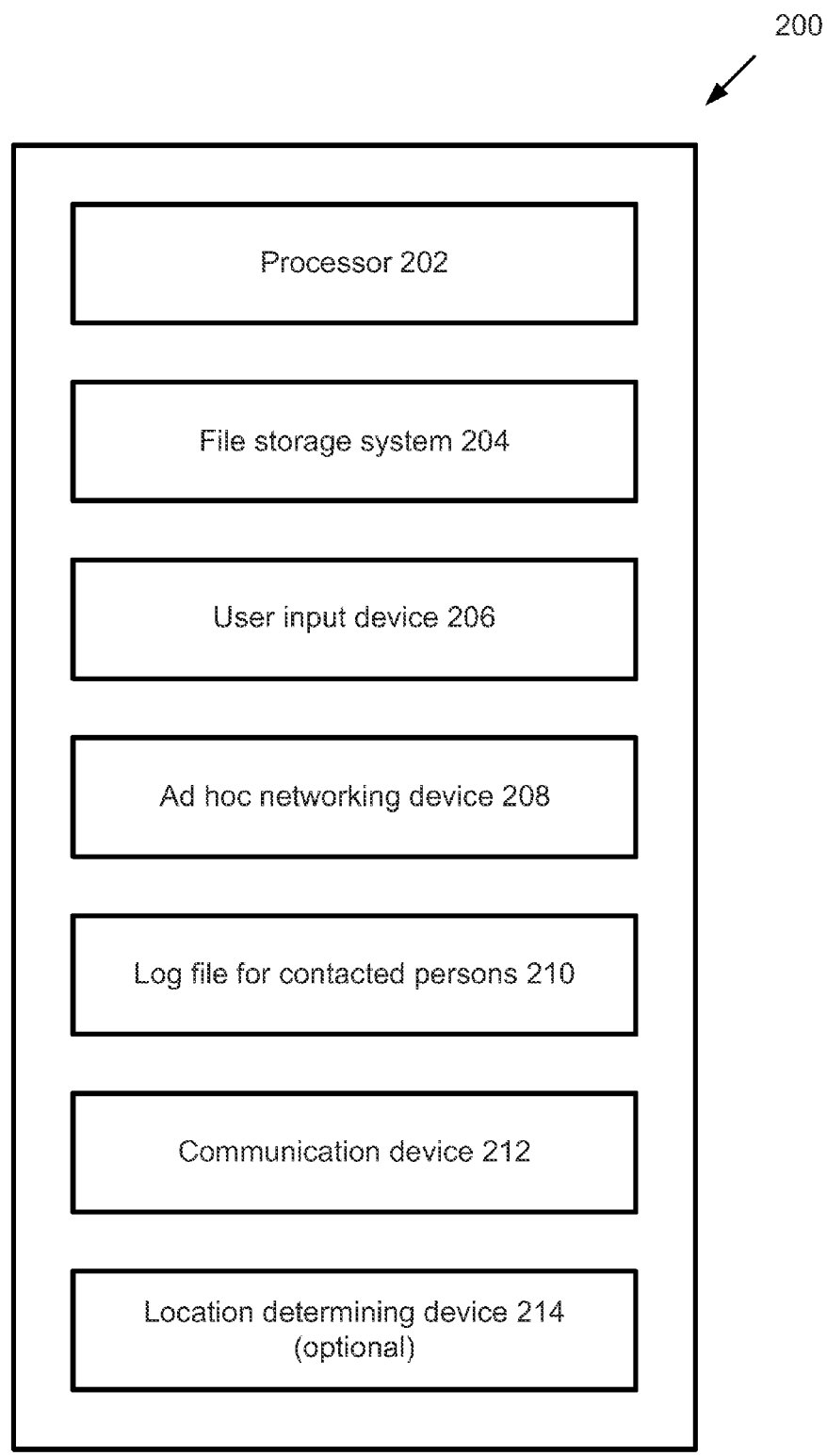
FIG. 2A is a schematic diagram illustrating functional blocks of an exemplary handheld computing and communication device.

FIG. 2A is a schematic diagram illustrating functional blocks of an exemplary handheld computing and communication device. The exemplary device 200 comprises a processor 202 that pertains to be a microprocessor or a microcontroller. The processor 202 may also include a DSP (Digital Signal Processor). The device 200 further comprises a file storage system 204. The file storage system may include one or multiple semiconductor memory devices such as flash memory devices. The file storage system may also include magnetic storage devices and optical disks. The file storage system may even comprise cache for reducing access time. The identity of the handheld device may be stored in the cache. The log file 110 is stored in the file storage system 204.

A user input device 206 is included in the device 200. The user input device includes keys, buttons, touch sensitive screens, touch pads, rotational user interafces and dials.

The device 200 further comprises an ad hoc networking device 208. The device 208 may be one or a combination of the communication device conforming to standards and their extensions including but not limiting to the Bluetooth (IEEE 802.11b), the ZigBee (IEEE 802.15.4), the Wi-Fi (IEEE 802.11) and the NFC (Near Field Communication). The device may further include a means of adjusting a coverage range of the ad hoc network controlled by the processor 202 through a program.

The device 200 includes a log file 210 for recording identities of the devices in the ad hoc networks. The log file 210 is controlled by a log file manager. The log file manager may be a program executable by the processor 202. The log file manager manages the log file 210 and may coordinate an operation of sending the log file to the central station after receiving an authorized signal.

The device 200 further comprises a communication device 212 for connecting the device to a communication network. The network may be a public telephone network. The network may also be the Internet.

The device 200 may also include a location determining device 214. The device 214 may be a GPS (Global Positioning System). The device 214 is used to determine the location of the device. The determined locations of the ad hock networks may also be stored in the log file. The device may comprise other means of determining location such as multilateration of radio signals as known in the art.

Figure 2B:
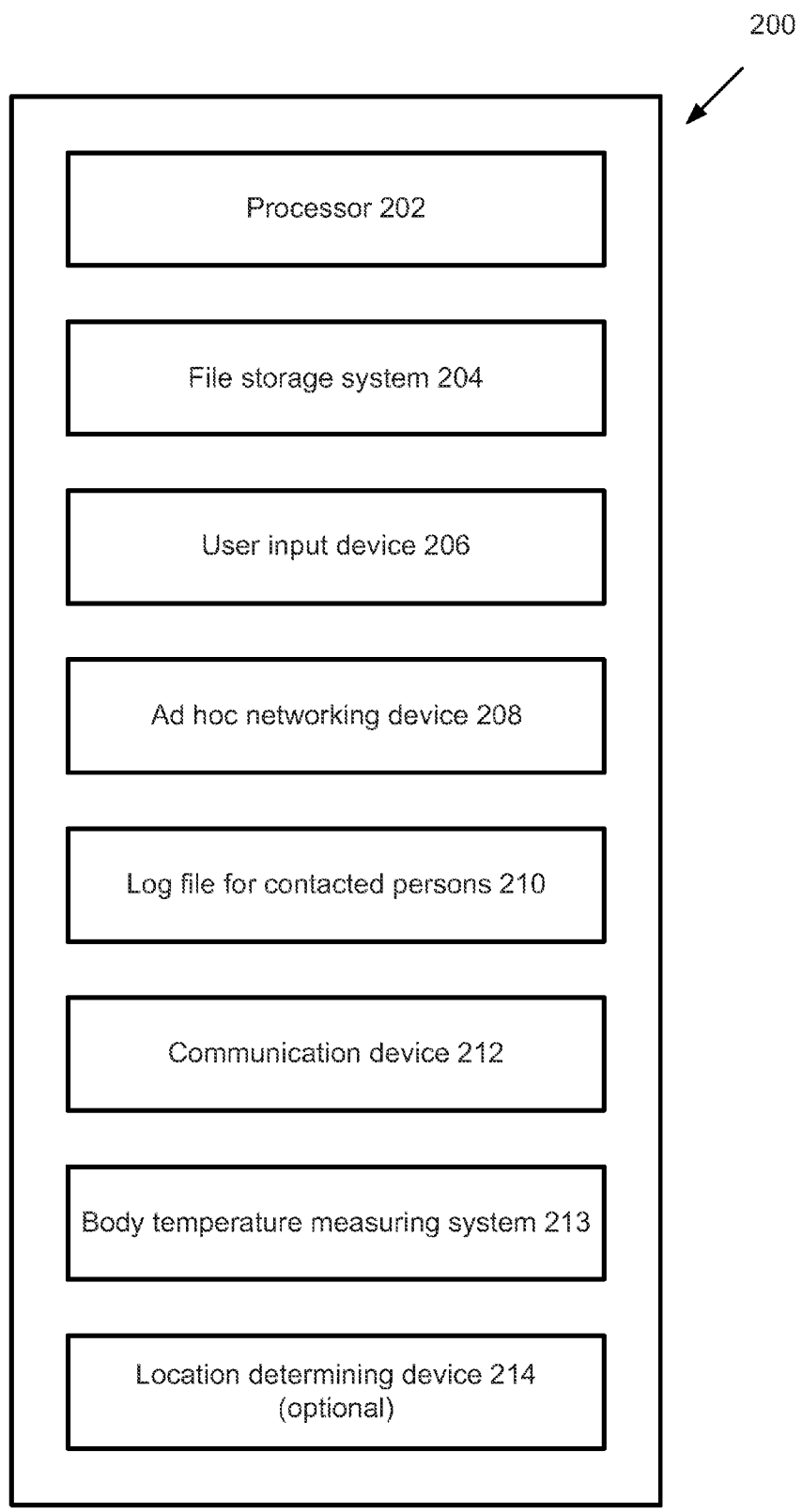
FIG. 2B is a schematic diagram illustrating functional blocks of an exemplary handheld computing and communication device including an automatic body temperature measuring system.

FIG. 2B is a schematic diagram illustrating functional blocks of another exemplary handheld computing and communication device 201. The device 201 includes an automatic body temperature measuring system 213. The automatic body temperature measuring system may include one or multiple temperature sensors. The sensors may be placed in selected locations of the handheld device. When the user holds the device, the body temperature may be measured and recorded. The system 213 may also include sensors for measuring ambient temperatures and, therefore, filtering out data points representing ambient but not the user's body temperatures. The temperature sensors may also be included in earpieces as shown in FIG. 1C. When the earpieces are plugged into ears of the user, the body temperature of the user may be taken automatically. The handheld device 201 may have a body temperature alerting means. If the body temperature of the user is in exceeding of a predetermined value, such as for example, 37.5 C, a signal will be sent to the processor 202 to trigger follow up actions including sending the body temperature data and the log file to the central station.

In an alternative implementation, the automatic temperature measuring system may include an infrared sensor to measure the body temperature of the user.

Figure 3A:
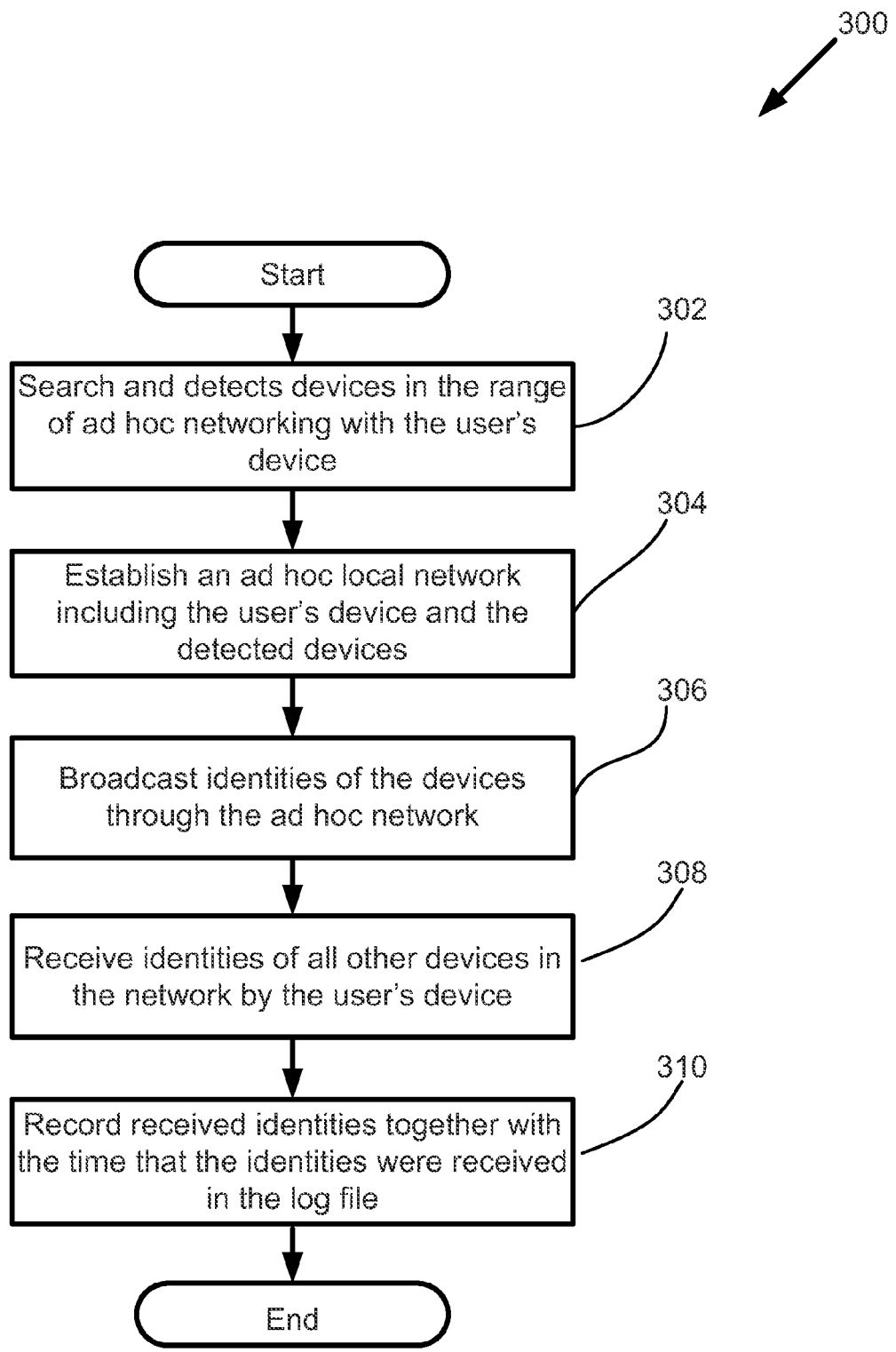
FIG. 3A is a flowchart illustrating operation of an exemplary system.

FIG. 3A is a flowchart illustrating operation of an exemplary system. Process 300 begins with step 302 that the networking device of the user's device searches and detects devices within reaching of the networking device. In step 304, an ad hoc communication network is established including the user's device and all devices detected. In step 306, identities of the devices are broadcasted through the network. In step 308, the user's device receives the identities of all other devices in the network. In step 310, the received identities together with a time that at least one of the identities is received are recorded in the log file. According to one aspect, both starting time and ending time of a device in the network may be recorded.

Figure 3B:
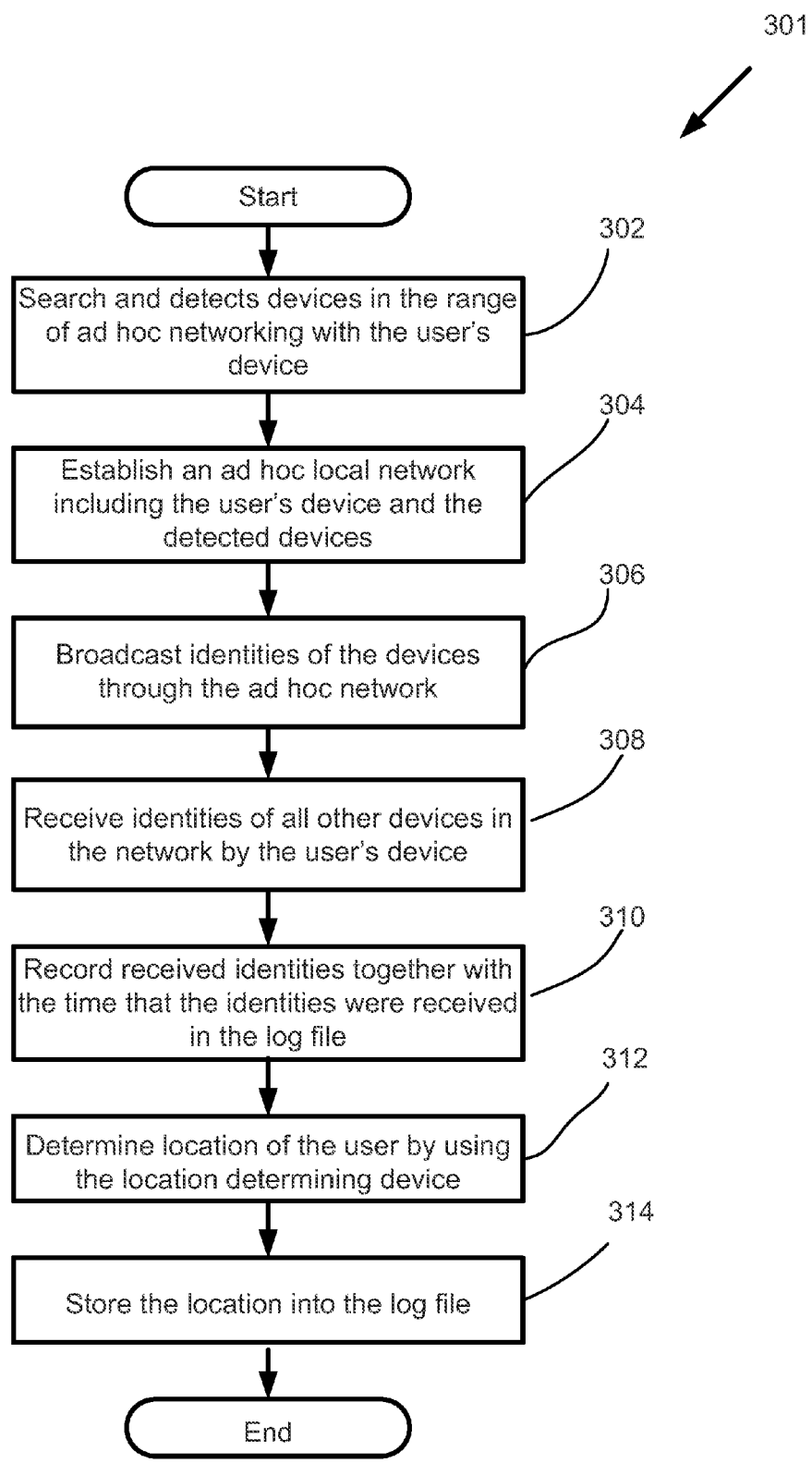
FIG. 3B is a flowchart illustrating operation of an exemplary system including a location determining device.

FIG. 3B is a flowchart illustrating operation of an exemplary system including a location determining device. Process 301 is identical to the process 300 except that a location determining device is utilized to determine the location of the ad hoc network in step 312. The location determining device may be a GPS in the user's device. In step 314, the measured location is recorded into the log file.

Figure 3C:
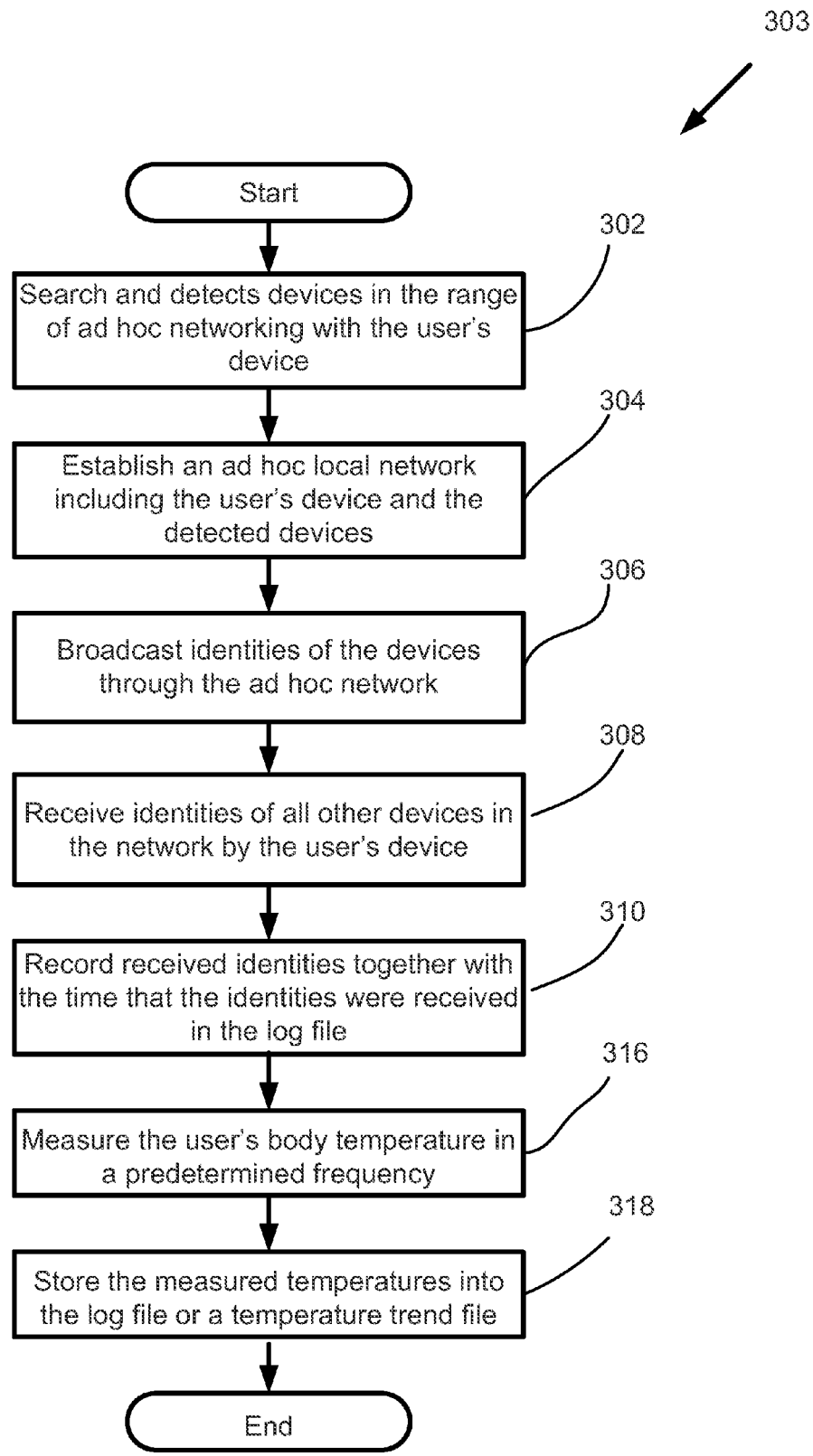
FIG. 3C is a flowchart illustrating operation of an exemplary system including the user's body temperature measurement.

FIG. 3C is a flowchart illustrating operation of an exemplary system including the user's body temperature measurement. Process 303 is identical to the process 300 except that body temperature of the user is measured in a predetermined frequency in step 316. According to one aspect of the present invention, the body temperature is measured by the user by using an external temperature measurement system and then is imported to the handheld device of the user. According to another aspect, the body temperature is measured by a temperature measurement system integrated with the device.

According to one implementation, the temperature sensors are placed in locations of the device that the user's hand is likely to be in touch with when the user operates the device. According to another implementation, the temperature sensors are placed in earpieces. When the user utilizes the earpieces, the body temperature can be measured automatically. The handheld device may further include temperature sensors for measuring the ambient temperature to make sure that the measured temperatures by the temperature sensors are indeed the user's body temperature but not the ambient temperatures. In step 318, the measured body temperatures are recorded either in the log file or in a separated temperature trend file. It should be noted that handheld devices may generate heat during operations. It may be necessary to isolate thermally the temperature sensors from a body of the handheld device in order that correct body temperatures of the user are taken.

Figure 4A:
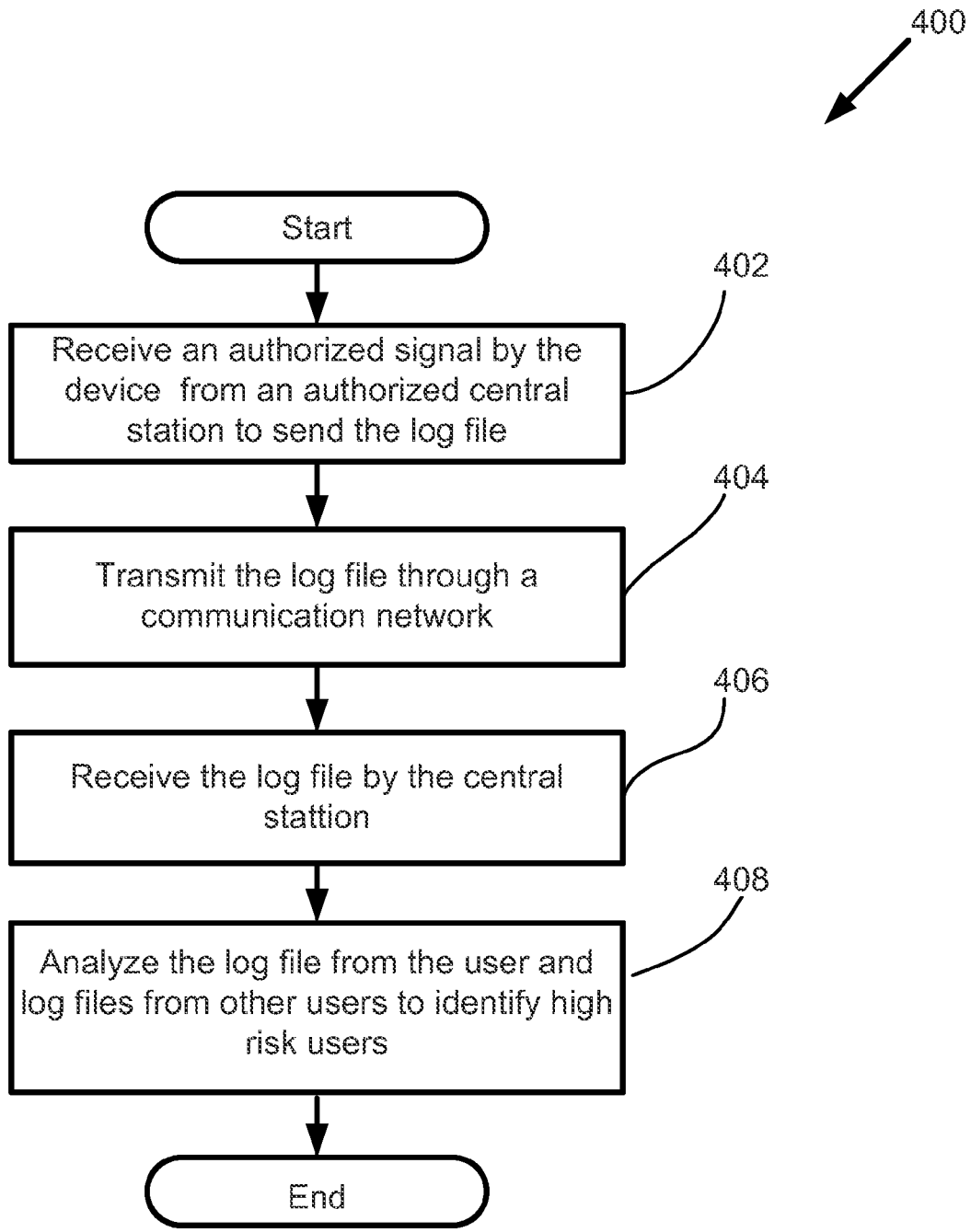
FIG. 4A is a flowchart illustrating operation of transmitting the log file to an authorized central station.

FIG. 4A is a flowchart illustrating operation of transmitting the log file to an authorized central station. Process 400 begins with step 402 that an authorized signal is received by the user's handheld device. The authorized signal may be from a central station. The signal may be transmitted through a public communication network, such as for example, through a telephone network or through the Internet. The central station may be controlled by a government agency. In the event of outbreak of a contagious disease, the agency may make a decision to collect the log files from selected group of citizens through the use of the handheld devices. For example, if a person is identified as infected, the log file in the person's handheld device is transmitted to the central station. All persons in contact with the infected persons within a predetermined period of time can be identified as potentially infected persons. Subsequently, by sending an authorized signal to the devices of the potentially infected persons, the next level of potentially infected persons can be identified.

Upon receiving the authorized signal, the log file stored in the user's handheld device is transmitted to the central station through a communication network in step 404. The communication network may be the same public communication network as the authorized signal was sent. The communication network may be a different network. In step 406, the log files are received by the central station. In step 408, the received log file from the user and other log files from the other users are analyzed. High risk users may be identified through the analysis.

According to another aspect of the present invention, the log file and the temperature trend file can be sent to the central station upon receiving the authorized signal.

Figure 4B:
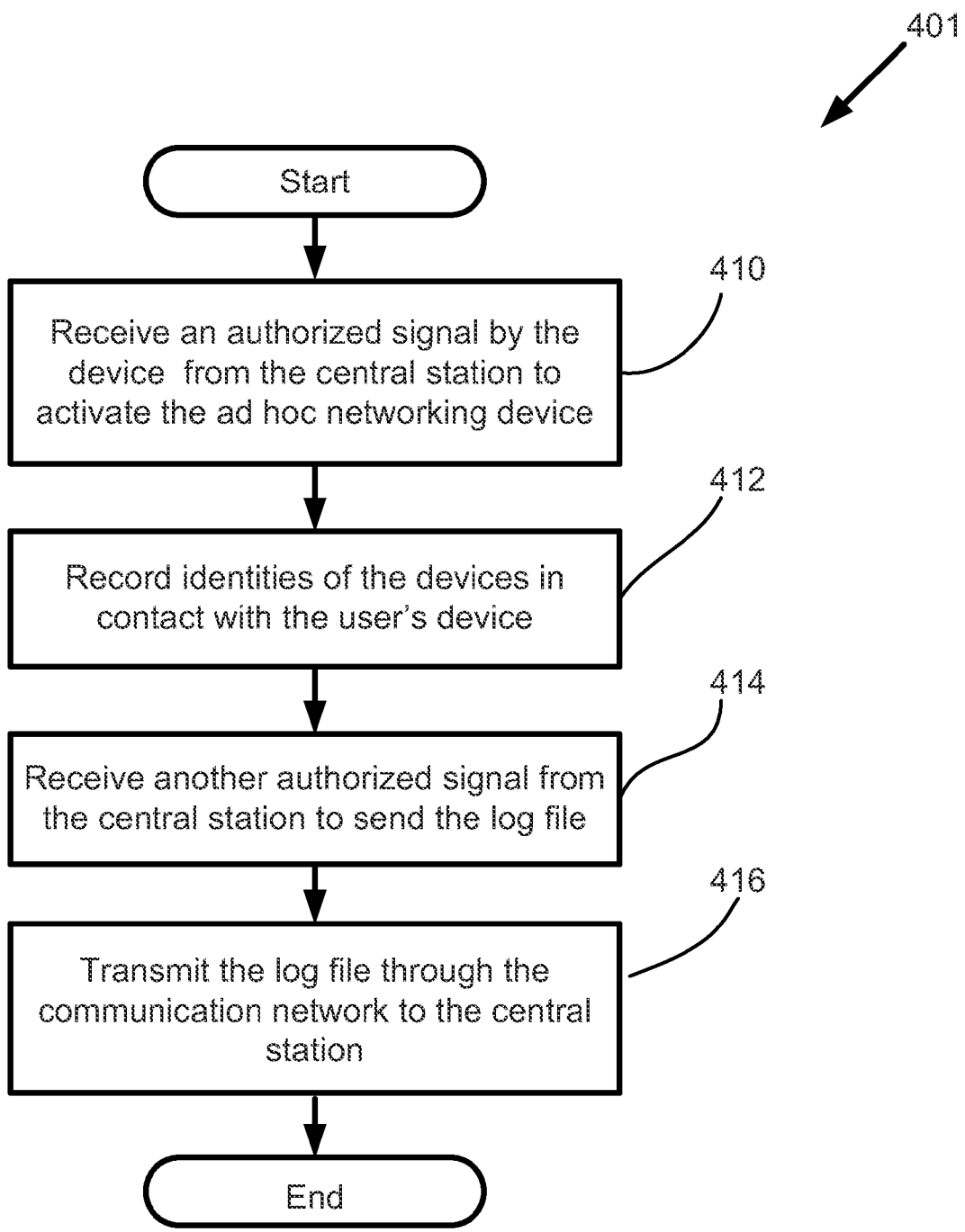
FIG. 4B is a flowchart illustrating operation of transmitting the log file to an authorized central station after activating of the ad hoc networking device.

FIG. 4B is a flowchart illustrating operation of transmitting the log file to an authorized central station after activation of the ad hoc networking device. Process 400 begins with step 410 that an authorized signal is received by the handheld device to activate the ad hoc networking device. In step 412, identities of devices in ad hoc networks are received and recorded in the log file. In step 414, another authorized signal is received to send the log file to the central station. In step 416, the log file is transmitted to the central station through the communication network. The temperature trend file may be sent at the same time.

Figure 5:
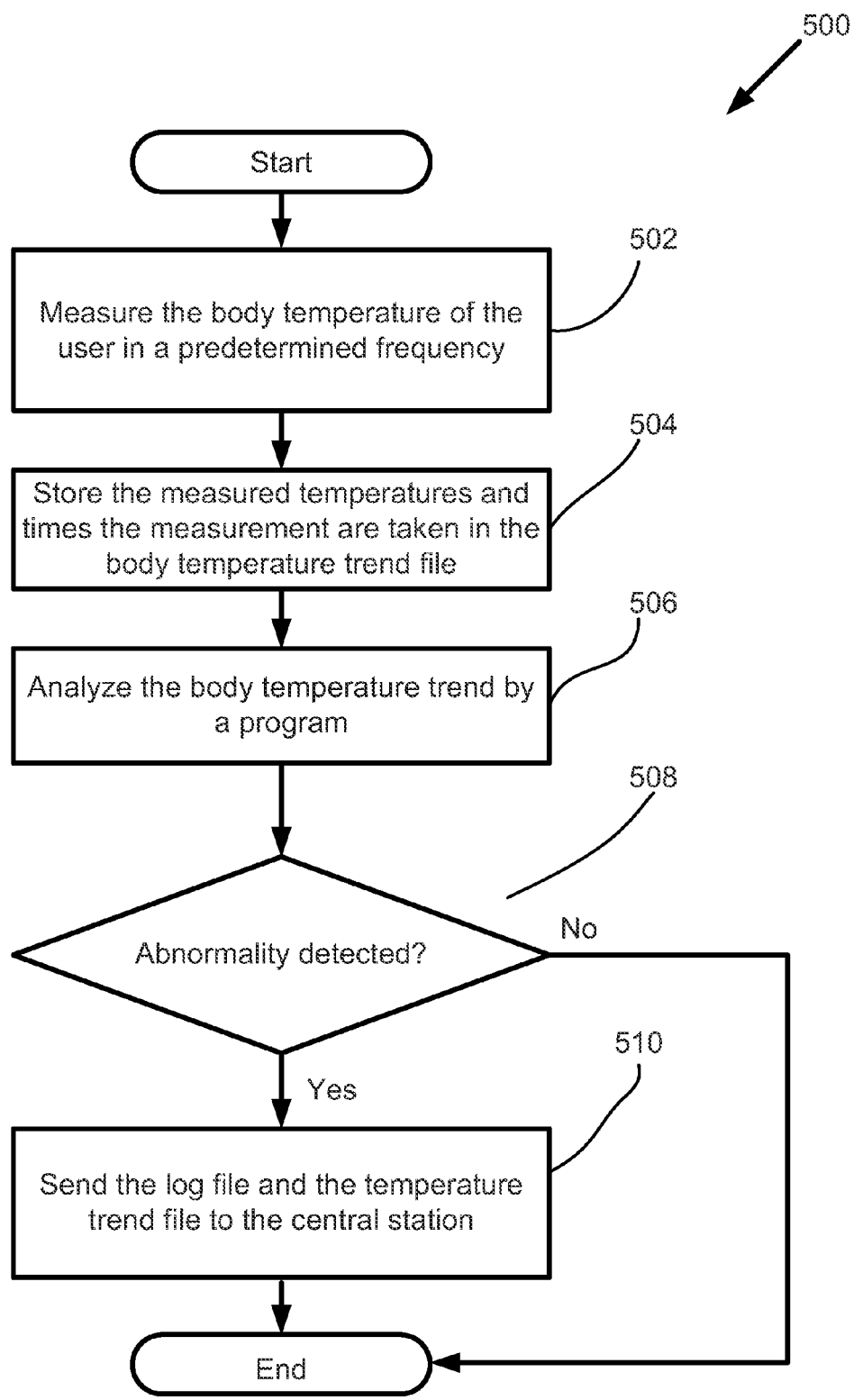
FIG. 5 is a flowchart illustrating operation of transmitting the log file to an authorized central station if the user's body temperature is in exceeding of a predetermined value.

FIG. 5 is a flowchart illustrating operation of transmitting the log file to an authorized central station if the user's body temperature is in exceeding of a predetermined value. Process 500 begins with step 502 that the user's body temperature is measured in a predetermined frequency by an automatic body temperature measuring system in the handheld device. The measured temperatures are stored in a body temperature trend file in step 504. The body temperature trend is analyzed by a program in step 506. The program judges in step 508 if abnormalities are detected. For example, if at least one of the measured body temperatures is in exceeding of a predetermined value, such as for example, 37.5 C, the log file and the temperature trend file (if it has not been included in the log file) are sent to the authorized central station in step 510.

Systems and methods are disclosed for monitoring outbreak of the contagious disease. The systems can be extended to other applications. For example, the systems may be employed to track persons contacted a terrorist or a criminal.

The invention claimed is:

1. A method of tracking a history of person-to-person interaction through the use of personal handheld computing and communication devices for monitoring outbreak of a contagious disease, the method comprising:
   (a) establishing an ad hoc communication network by a plurality of handheld computing and communication devices when said handheld devices are within a predetermined distance in a location, each of said personal handheld devices is stored with an identity associated with each of users;
   (b) broadcasting each of the identities by each of said handheld devices through said ad hoc communication network;
   (c) receiving and recording in a log file by each of said handheld devices all other identities of other handheld devices;
   (d) receiving an authorized signal by at least one of said handheld devices from a central station through a communication network; and
   (e) transmitting the log file in said one of said plurality of handheld devices to the central station through the communication network,
      wherein said predetermined distance is adjustable by a program stored in said handheld devices, wherein said predetermined distance is determined by nature of the contagious disease.

2. The method as recited in claim 1, wherein said identities of the users are encrypted.

3. The method as recited in claim 2, wherein said encrypted identities can only be decrypted by an authorized agency after receiving the log file by the central station.

4. The method as recited in claim 1, wherein said method further comprising storing a time that the identities are received at the location.

5. The method as recited in claim 1, wherein said method further comprising:
   (a) determining the location of the ad hoc network by a location determining device; and
   (b) recording the location into the log file.

6. The method as recited in claim 1, wherein said method further comprising:
   (a) measuring body temperatures of at least one of said users by a temperature sensor in the handheld device in a predetermined frequency;
   (b) recording the measured temperatures in a temperature trend file; and
   (c) transmitting the temperature trend file together with the log file to said central station after receiving the authorized signal.

7. The method as recited in claim 6, wherein said body temperatures are measured by the temperature sensor automatically.

8. The method as recited in claim 6, wherein said temperature sensor is located in an earpiece, wherein said earpiece has functionalities of delivering sound signals and measuring the body temperature automatically.

9. The method as recited in claim 1, wherein said ad hoc network conforms to one or a combination of the following standards:
   (a) Wi-Fi
   (b) Bluetooth;
   (c) ZigBee; and
   (d) NFC (Near Field Communication).

10. The method as recited in claim 1, wherein said handheld devices further comprising one or a combination of following devices:
    (a) a media player;
    (b) a mobile phone;
    (c) a tablet computer;
    (d) a laptop computer; and
    (e) a digital camera.

11. A method of tracking a history of person-to-person interaction through the use of personal handheld computing and communication devices for monitoring outbreak of a contagious disease, the method comprising:
    (a) receiving an authorized signal by a plurality of handheld computing and communication devices from a central station through a communication network;
    (b) activating ad hoc networking devices in said handheld devices;
    (c) establishing an ad hoc communication network by a plurality of handheld computing and communication devices when said handheld devices are within a predetermined distance in a location, each of said personal handheld devices is stored with an identity associated with each of users;
    (d) broadcasting each of the identities by each of said handheld devices through said ad hoc communication network;
    (e) receiving and recording in a log file by each of said handheld devices all other identities of other handheld devices;
    (f) receiving an authorized signal by at least one of said handheld devices from a central station through a communication network; and
    (g) transmitting the log file in said one of said plurality of handheld devices to the central station through the communication network,
       wherein said predetermined distance is adjustable by a program stored in said handheld devices, wherein said predetermined distance is determined by nature of the contagious disease.

12. The method as recited in claim 11, wherein said method further comprising:
    (a) determining the location of the ad hoc network by a location determining device; and
    (b) recording the location into the log file.

13. The method as recited in claim 11, wherein said method further comprising:
    (a) measuring body temperatures of at least one of said users by a temperature sensor in the handheld device in a predetermined frequency;
    (b) recording the measured temperatures in a temperature trend file; and
    (c) transmitting the temperature trend file together with the log file to said central station after receiving the authorized signal.

14. The method as recited in claim 13, wherein said body temperatures are measured by the temperature sensor automatically.

15. The method as recited in claim 13, wherein said temperature sensor is located in an earpiece, wherein said earpiece has functionalities of delivering sound signals and measuring the body temperature automatically.

16. A method of tracking a history of person-to-person interaction through the use of personal handheld computing and communication devices for monitoring outbreak of a contagious disease, the method comprising:
  (a) establishing an ad hoc communication network by a plurality of handheld computing and communication devices when said handheld devices are within a predetermined distance in a location, each of said personal handheld devices is stored with an identity associated with each of users;
  (b) broadcasting each of the identities by each of said handheld devices through said ad hoc communication network;
  (c) receiving and recording in a log file by each of said handheld devices all other identities of other handheld devices;
  (d) recording in a temperature tend file body temperatures of at least one of said users by a temperature sensor in the handheld device associated with said one of the users;
  (e) analyzing the recorded temperatures by a processor of the handheld device; and
  (f) transmitting the log file and the temperature trend file to the central station through the communication network if an abnormality of the recorded temperatures is detected,
    wherein said predetermined distance is adjustable by a program stored in said handheld devices, wherein said predetermined distance is determined by nature of the contagious disease.

17. The method as recited in claim 16, wherein said temperature sensor is placed in selected positions including in earpieces of the handheld device, wherein said earpieces have functionalities of delivering sound signals and measuring the body temperature automatically.

18. The method as recited in claim 16, wherein said temperature sensor further comprising infrared sensors.

* * * * *